US005645072A

United States Patent [19]
Thrall et al.

[11] Patent Number: 5,645,072
[45] Date of Patent: Jul. 8, 1997

[54] REAL TIME CHEMICAL EXPOSURE AND RISK MONITOR

[76] Inventors: Karla D. Thrall, 3804 Alder Lake Ct., West Richland, Wash. 99353; Donald V. Kenny, 6947 Sparrow La., Worthington, Ohio 43235; George W. R. Endres, 2112 Briarwood Ct., Richland, Wash. 99352; Daniel R. Sisk, 1211 Marshall Ave., Richland, Wash. 99352

[21] Appl. No.: 535,929

[22] Filed: Sep. 28, 1995

[51] Int. Cl.$^6$ .................................................. A61B 5/09
[52] U.S. Cl. .......................... 128/719; 128/716; 128/725
[58] Field of Search .................................. 128/716, 714, 128/730, 727, 204.17, 206.21

[56] References Cited

U.S. PATENT DOCUMENTS

| Re. 34,938 | 5/1995 | Serikov et al. | 128/716 |
| 3,759,249 | 9/1973 | Fletcher et al. | 128/719 |
| 3,834,375 | 9/1974 | Sanctuary et al. | 128/719 |
| 3,985,017 | 10/1976 | Goldsmith . | |
| 4,756,670 | 7/1988 | Arai | 128/719 |
| 5,042,501 | 8/1991 | Kenny et al. | 128/719 |
| 5,111,827 | 5/1992 | Rantala | 128/719 |

OTHER PUBLICATIONS

Angela D. Arms, and Curtis C. Travis (U.S. Environmental Protection Agency); "Reference Physiological Parameters in Pharmacokinetic Modeling"; *EPA Final Report #EPA/600/6-88/004*; (Feb. 1988); pp. i through 7-16.

PH Dawson, JB French, JA Buckley, DJ Douglas, and D. Simmons; "Mass Spectrometry, 1–The Instrument Parameters"; *J. of Organic Mass Spectrometry*, vol. 17, No. 5; (1982); pp. 205-211.

PH Dawson, JB French, JA Buckley, DJ Douglas, D. Simmons; "The Use of Triple Quadrupoles for Sequential Mass Spectrometry, 2–A Detailed Case Study"; *J. of Organic Mass Spectrometry*, vol. 17, No. 5; (1982); pp. 212-219.

James A. Bond, Lance A. Wallace, Siv Osterman–Golkar, George W. Lucier, Alan Buckpitt, and Rogene F. Hendersen; "Symposium Overview Assessment of Exposure to Pulmonary Toxicants: Use of Biological Markers"; *J or Fundamental and Applied Toxicology*, vol. 18; (1992); pp. 161–174.

Dennis J. Paustenbach, Harvey J. Clewell III, Michael L. Gargas, and Melvin E. Andersen; "A Physiologically Based Pharmacokinetic Model for Inhaled Carbon Tetrachloride"; *J. of Toxicology and Applied Pharmaclogy*, vol. 96; (1988); pp. 191–211.

Michael L. Gargas, Melvin E. Andersen and Harvey J. Clewell III; "A Physiologically Based Simulation Approach for Determining Metabolic Constants from Gas Uptake Data"; *J. of Toxicology and Applied Pharmacology*, vol. 86; (1986); pp. 341–352.

John C. Ramsey and Melvin E. Andersen; "A Physiologically Description of the Inhalation Pharmacokinetics of Styrene in Rats and Humans"; *J. of Toxicology and Applied Pharmacology*, vol. 73; (1984); pp. 159–175.

Michael L. Gargas, Harvey J. Clewell III, and Melvin E. Andersen; "Metabolism of Inhaled Dihalomethanes In Vivo: Differentiation of Kinetic Constants for Two Independent Pathways"; *J. of Toxicology and Applied Pharmacology*, vol. 82; (1986); pp. 211–223.

(List continued on next page.)

*Primary Examiner*—Lee S. Cohen
*Assistant Examiner*—Stephen Huane
*Attorney, Agent, or Firm*—Paul W. Zimmerman

[57] ABSTRACT

The apparatus of the present invention is a combination of a breath interface and an external exposure dosimeter interface to a chemical analysis device, all controlled by an electronic processor for quantitatively analyzing chemical analysis data from both the breath interface and the external exposure dosimeter for determining internal tissue dose. The method of the present invention is a combination of steps of measuring an external dose, measuring breath content, then analyzing the external dose and breath content and determining internal tissue dose.

21 Claims, 6 Drawing Sheets

OTHER PUBLICATIONS

Kent W. Thomas, Edo D. Pellizzari, and Stephen D. Cooper; "A Canister–Based Method for Collection and GC/MS Analysis of Volatile Organic Compounds in Human Breath"; *J. of Analytical Toxicology,* vol. 15; (Mar./Apr. 1991); pp. 54–59.

JH Raymer, KW Thomas, SD Cooper, DA Whitaker, and ED Pellizzari; "A Device for Sampling of Human Alveolar Breath for the Measurement of Expired Volatile Organic Compounds"; *J. of Analytical Toxicology,* vol. 14; (Nov./Dec. 1990); pp. 337–344.

REAL TIME CHEMICAL EXPOSURE AND RISK MONITOR

This invention was made with Government support under Contract DE-AC06-76RLO 1830 awarded by the U.S. Department of Energy. The Government has certain rights in the invention.

FIELD OF THE INVENTION

The present invention relates generally to a method and apparatus for determining internal tissue dose of airborne volatile contaminant exposure. More specifically, the apparatus of the present invention is a combination of a breath interface and an external exposure dosimeter interface to a mass spectrometer, all controlled by a computer together with a software module for analyzing data from both the breath interface and the external exposure dosimeter for determining internal tissue dose. The method of the present invention is a combination of steps of measuring an external dose, measuring breath content, then analyzing the external dose and breath content and determining internal tissue dose.

BACKGROUND OF THE INVENTION

Observation of industrial hygiene has substantially improved working environments in the recent past. Nevertheless, accidental and unavoidable exposures occur and the need to assess these exposures remains.

Physiologically based pharmacokinetic (PBPK) models are frequently used to describe the biokinetics of a chemical in experimental animals, and can be used to predict human tissue levels of a hazardous chemical following exposure. The process of developing a PBPK model typically includes validation studies to experimentally test model assumptions and hypotheses. A validation study generally involves monitoring a biomarker, or a change in the biological system that can be related to an exposure or effect from a toxic agent. Common biomarkers include the presence of the parent compound and/or metabolites in blood, in exhaled breath, or in excreted urine or feces.

Analysis of exhaled breath represents a non-invasive method for detecting exposure to a particular toxicant. Breath measurements are useful in environmental exposure studies, and may provide evidence about previous long-term or repeated exposures in environments that are not easy to monitor (Bond et al. 1992). If breath samples are collected during, or immediately following, a short-term exposure, breath measurements can be used to predict the peak exposure. Previous breath-sampling methodologies have been to collect repeated 1-min breath samples at 5-min intervals (Raymer et al. 1990). Although this method can aid in describing the rapid exponential emptying of the blood compartment that occurs immediately following peak exposure, sampling in 5-min intervals still forces an approximation of the true shape of the clearance kinetics. This is because people breath at a rate of about 20 breaths per minute.

Presently, personnel wear an external exposure dosimeter commonly known as a lapel chemical sampler (lapel pin) that is a small glass or metal hollow vial or tube in the shape of a cylinder, the tube having a chemical sorbent coated on the internal wall surface. As air passes through the tube, any chemical compatible with the sorbent is sorbed thereon for quantification by later desorbtion and chemical analysis, for example by a gas chromatograph mass spectrometer. In addition, personnel exhale into a plastic bag that is sealed, then later quantified by chemical analysis in a mass spectrometer. The identified chemicals and concentrations of each chemical may be entered into a physiologically based pharmacokinetic (PBPK) algorithm programmed on a computer. The result or output of the computer analysis is an estimate of internal tissue dose.

Presently, the external exposure dosimeter or lapel pin and breath samples are sent to a central laboratory for chemical analyses and subsequent quantitative analyses. These analyses require about 4–8 weeks on a routine basis and if there is a known emergency, require about 24 hours. This time lag between exposure and analysis is significant for at least three reasons. First, if an exposure requires treatment, the treatment is delayed by the amount of time for analysis, and second, the analysis uncertainty is greater with increased time between actual exposure and chemical analysis of that exposure. Thirdly, the use of the separate single-point measurements of breath and external dosimeter is inadequate for quantitatively assessing the total integrated exposure, dose, and predicted response of a worker exposed to hazardous chemicals. Previously reported batch collection methods (Thomas et al. 1991), such as collection of samples on sorbents or in canisters, integrate or average the concentration data over the collection or sampling period and may miss vital trend data.

Hence, there is a need for a method and apparatus that would provide real time chemical and quantitative analyses of internal tissue dose.

Background References

1. Bond, J. A., Wallace, L. A., Osterman-Golkar, S., Lucier, G. W., Buckpitt, A., and Hendersen, R. F. (1992). Assessment of exposure to pulmonary toxicants: Use of biological markers. *Fundam. Appl. Toxicol.* 18, 16–174.
2. Raymer, J. H., Thomas, K. W., Cooper, S. D., Whitaker, D. A., and Pellazzari, E. D. (1990). A device for sampling human alveolar breath for measurement of expired volatile organic compounds. *J. Anal. Toxicol.* 14, 337–344.
3. Thomas, K. W., Pellazzari, E. D., and Cooper, S. D. (1991). A canister-based method for collection and GC/MS analysis of volatile organic compounds in human breath. *J. Anal. Toxicol.* 15, 54–59.

SUMMARY OF THE INVENTION

The apparatus of the present invention is a combination of a breath interface and an external exposure dosimeter interface to a mass spectrometer for chemical analyses, all controlled by a computer, together with a software module for quantitatively analyzing chemical analysis data from both the breath interface and the external exposure dosimeter for determining internal tissue dose. The method of the present invention is a combination of steps of measuring an external dose, measuring breath content, then analyzing the external exposure and breath content, and determining internal tissue dose.

The present invention permits obtaining data from each exhaled breath sequentially over a period of at least one minute, or for about 20 exhaled breaths for a person. Having data for each exhaled breath in sequence and in real time permits greater accuracy in determining the shape of the clearance kinetics curve. Further, greater accuracy in determining peak exposure is also achieved.

Using experimental animals, we have demonstrated the feasibility of calibrating a PBPK model by monitoring the real-time exhalation of a biomarker of exposure. In more complex exposure and modeling situations, the collection of real-time kinetic data will permit modification of key model parameters, for example, gastrointestinal tract absorption rates following volatile compounds. A real advantage to monitoring samples collected in real-time is trends in the changing matrix may be tracked. Furthermore, the use of the relatively sophisticated tandem-mass spectrometric techniques results in sensitive (i.e., ppb) analysis of many compounds of interest in real time. These techniques are useful for non-invasive monitoring and tracking the real-time evolution of metabolites and volatile biomarkers of effect following exposure. This has many potentially valuable applications in PBPK modeling, basic research, and human health risk assessment.

It is an object of the present invention to provide a method and apparatus for a near real time determination of internal tissue dose.

It is a further object of the present invention to provide combined measurements of breath and an external dosimeter that are adequate for quantitatively assessing the total integrated exposure, dose, and predicted health risk of a worker exposed to hazardous chemicals.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
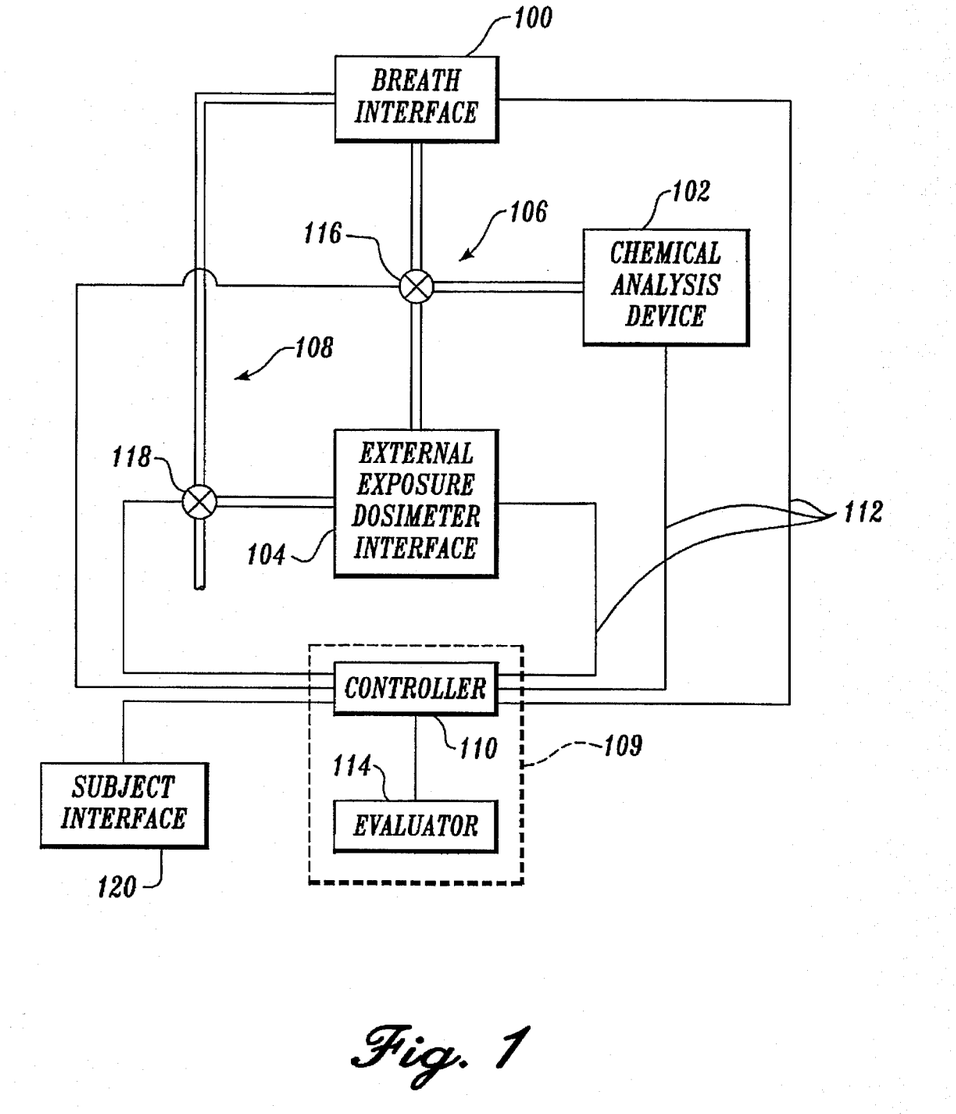
FIG. 1 is a schematic of the breath analysis system.

A new analysis system has been developed to monitor the real-time exhalation of volatile compounds from animals and humans as shown in FIG. 1. The exhalation data are collected using a breath interface 100, described in U.S. Pat. No. 5,042,501 herein incorporated by reference, that links the exhaled breath directly into a chemical analysis device 102. Exposure data are collected by an external exposure dosimeter interface 104. The breath interface 100 and external exposure dosimeter interface 104 are connected to a common inlet 106 to the chemical analysis device 102. A gas purge line 108 is also connected to the breath interface 100 and the external exposure dosimeter interface 104. Air flow signals and chemical analysis signals are sent to an electronic processor 109 via wires 112. The electronic processor 109 contains a controller 110. Data from the controller 110 are sent to the evaluator 114 for modelling and risk analysis.

The breath interface 100 and the external exposure dosimeter interface 104 may be exchangeably connected to the chemical analysis device 102, but are preferably connected to a common inlet 106 having a selection valve 116. The selection valve 106 may be a single 3-port or 3-way valve, or it may be two dual-port or 2-way valves with an intervening tee fitting. The selection valve 106 may include three or more valves for isolation purposes.

A selector valve 118 is provided on the gas purge line 108 permitting purging of one or both of the breath interface 100 and the external exposure dosimeter interface 104 at a time.

A subject interface 120 is a series of instructions for a person to operate the analysis system. The instructions are preferably either a computer display, or other lit display responsive to sensors so that instructions are displayed or highlighted sequentially as the person performs each task in the instructions. Additionally, the subject interface may include a badge reader or other automated identification device.

Figure 2A:
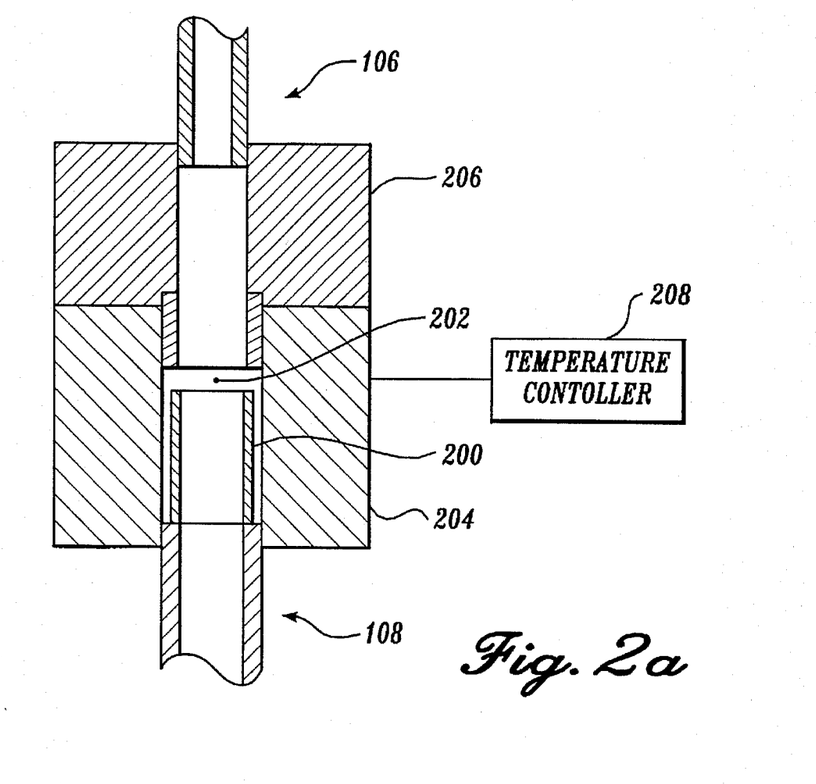
FIG. 2a is a cut-away of the external exposure dosimeter interface.

The external exposure dosimeter interface 104 is shown in further detail in FIG. 2a. A lapel tube 200 is inserted into a chamber 202 of a heating block 204. The lapel tube 200 is held in the chamber 202 by a desorption handle 206. The heating block 204 is heated and maintained at a preselected temperature by the temperature controller 208 while purge gas is introduced through the purge line 108. The purge gas entrains chemical compounds from the heated lapel tube 202 and enters the common inlet 106. The lapel tube 202 contains a sorbent media, known in the art of gas sampling, packed inside of the lapel tube 202. The lapel tube 202 may be made of any material, but is preferably glass or metal, and most preferably stainless steel. The lapel tube 202 may be of any hollow cross sectional shape, but is preferably a circular cylinder.

Figure 2B:
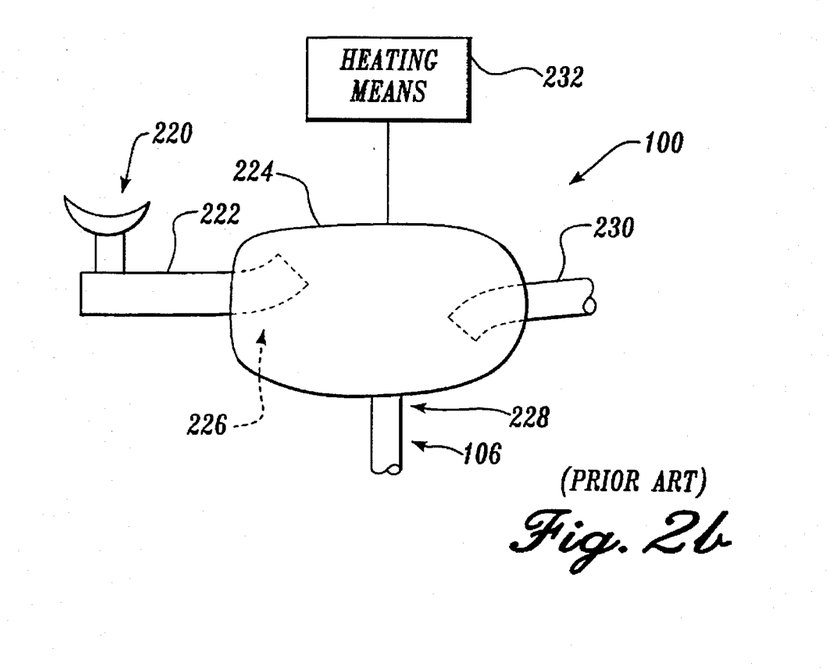
FIG. 2b is a sketch of the breath interface.

The breath interface 100 is shown in FIG. 2b. It has a mouthpiece 220 for interfacing a person to receive a breath. It further has a tube 222 for carrying exhaled breath from the mouthpiece 220 to a mixing chamber 224 having an inlet 226, outlet 228 and exit tube 230. The mixing chamber 224 provides a residence time sufficient to mix the breath and provide sufficient breath sample amount to the chemical analysis device 102, and provides a reservoir volume to absorb pulsation from inhalation and exhalation. A heating means 232 is provided to prevent condensation of vapor present in the breath sample. Further details of the breath interface 100 are found in U.S. Pat. No. 5,042,501.

The chemical analysis device 102 may be any chemical analysis device capable of receiving a gas sample and identifying chemical compounds entrained in the gas sample and capable of quantifying concentrations of said chemical compounds. Preferably, the chemical analysis device 102 is a mass spectrometer, specifically, a Teledyne 3DQ with a Teledyne firmware communication tower that collects data as binary information.

The electronic processor 109 may be one or more computers. The controller 110 and the evaluator 114 may be separate computers containing appropriate software instructions for performing their functions, or they may be software instruction sets residing on a single computer.

The controller 110 is an 80486 DX computer with a software program that converts the binary information to ASCII information. The ASCII information is in x,y pairs of time and concentration and is placed in a format compatible with the evaluator 114. The ASCII format is preferred so that data is more easily and reliably transmitted over a phone line. It will be apparent to one skilled in the art of data transfer that data could be collected on a disk or tape and manually transferred. In operation, the controller 110 initializes the system resetting variables from any previous analysis, and operates the selector valve 118 and the selection valve 116 for air purging the system. The controller then collects data from a new person, including breath data and external dosimeter data generated by the chemical analysis device 102, formats the data, and transmits the data to the evaluator 114. The controller also activates and responds to the subject interface 120. The controller 110 performs calibration of the chemical analysis device 102 and measures background response of the chemical analysis device 102. Additional data transmitted to the evaluator 114 includes identification of sample, date and time sample was taken, weight of person, and amount of time the person was in a defined zone.

The weight of a person is preferably measured automatically while the breath sample is obtained. Any well known automatic scale may be used to obtain the weight. Alternatively, a beam balance scale, or a spring scale with a readable dial, may be used wherein the person enters a weight manually.

The evaluator 114 is preferably a Unix workstation connected to a desktop or laptop computer. The Unix workstation runs the PBPK model, and the computer provides model inputs and serves as a receiver of PBPK model output.

Because the breath interface - mass spectrometer combination generates a new data point approximately every second, this apparatus can measure the rapid exponential emptying of the blood compartment that occurs immediately following peak exposure. Furthermore, coupling the real-time collection of biokinetic data with a physiologically descriptive toxicokinetic model permits elucidating complex in situ chemical-mediated biological reactions, particularly for rapidly occurring processes.

In operation, it is important to obtain chemical data from each exhaled breath in sequence. For a rat breathing at a rate of 120 breaths per minute, data must be taken about each second. For a person breathing at a rate of about 20 breaths per minute, data collected every 1.5 seconds is more than adequate.

PBPK Model

The PBPK model developed for $CCl_4$ was based on an earlier model developed by Paustenbach et al. (1988) to describe the uptake and retention of $CCl_4$ in rats, monkeys, and humans exposed via inhalation. The Paustenbach et al. model is a modification of the mass-balance equations that constitute the basic PBPK model originally described by Ramsey and Andersen (1984) to include multi-day exposure and to model the small metabolism chamber used to collect exhaled $^{14}CCl_4$. The kinetics of metabolism in the Paustenbach et al. model were determined by gas uptake studies, as described by Gargas et al. (1986a). Model parameters are substantially identical to those given by Paustenbach et al. (1988).

The PBPK models are preferably solved using SimuSolv (Dow Chemical Company, Midland, Mich.), a software package containing routines for numerical integration, optimization, and graphical display.

EXAMPLE 1

An experiment was conducted using laboratory rats to demonstrate a portion of the apparatus and method of the present invention.

The utility of this new methodology is illustrated using carbon tetrachloride ($CCl_4$) as a demonstration compound. An existing PBPK model was taken from the literature, Paustenbach et al. (1988), and modified to simulate an intravenous route of $CCl_4$ exposure in the male Fischer 344 rat. This PBPK model for the rat accurately described the concentrations of $CCl_4$ in real-time exhaled breath data collected from rats exposed to $CCl_4$ via a single intravenous injection.

Animals

Male, Fischer 344 rats, weighing 225–275 g, were purchased either with, or without, indwelling jugular vein cannulas from Charles River, Inc., Raleigh, N.C. Animals were housed singularly in solid-bottom cages with hardwood chips, and were acclimated on a 12-hr light/dark cycle prior to use. Rodent chow (NIH-07) and water were provided ad libitum throughout the acclimation period. Cannulas were maintained by periodic flushing with heparinized saline.

Intravenous Exposure and Sample Collection

In three different experiments, either two or four animals were placed in nose-only restraint tubes (C. H. Technologies, Westwood, N.J.) with access slots that allow the cannulas to be exteriorized from the animal. Each animal restrainer was connected via a nose port to the rat manifold. The exhaled breath from the rat exited the nose port and was driven into a common mixing chamber by a continuous flow of supplied breathing air. Samples for analysis by the mass spectrometer were continually drawn from the contents of the mixing chamber. Rats placed in restraint tubes are connected to the manifold. The exhaled breath from each animal is passed into a common heated mixing chamber, where the mass spectrometer draws a sample via a drying tube.

Each animal received a single intravenous injection of $CCl_4$ in isotonic saline, either through the Jugular vein cannula, or via the tail vein. In the first experiment, two animals were utilized, each receiving a dose of 0.6 mg/kg body weight (BW) (250 µl volume) through the jugular vein cannula. Cannulas were flushed with saline immediately following injection. The second and third experiments utilized 4 animals each, with each animal receiving a dose of 1.5 mg/kg BW (1 ml volume) through the tail vein. In all cases, the length of time of injection was approximately 1 minute. The combined exhaled breath from the exposed animals was measured continuously to determine the concentration of $CCl_4$ exhaled. The resulting concentration data were adjusted to account for dilution by the flow of supplied breathing air and divided by the number of rats to allow expression as ng $CCl_4$/l air per rat.

Breath-Analysis Instrumentation

The expired breath from the rats was monitored by interfacing the rats to a tandem mass spectrometer. The manifold was a modification of a human breath interface patented by Kenny and Kelly (1991) U.S. Pat. No. 5,042,501 herein incorporated by reference. This device can accommodate up to six rats connected by the nose-only restraint tubes mentioned above. Breathing air (1000 ml/min) is constantly supplied to the rats through the center tube (175 ml volume) of the manifold at a rate greater than the combined ventilation rate of the animals on the system, and can be adjusted for the number of rats being monitored. Re-breathing of the exhaled air was considered to be negligible. The exhaled breath from each rat flows into a common heated mixing chamber (300 ml volume) from which the mass spectrometer continuously draws its sample. The excess exhaled air is vented from the mixing chamber with negligible flow restriction via a large bore hole exit tube. Intensity data from the mass spectrometer was converted to concentration (ppb) through the use of external standards and a calibration curve for carbon tetrachloride. A new calibration curve was generated each day of experimentation.

During these experiments, the expired breath of the rats was monitored in real-time using a Sciex Trace Atmospheric Gas Analyzer (TAGA) 6000E tandem mass spectrometer (Sciex, Thornhill, Ontario, Canada) equipped with a low-pressure chemical ionization source (LPCI). The TAGA combines sampling and analysis into one rapid operation, while maintaining a very high level of sensitivity and selectivity (Dawson et al. 1982a; 1982b). The TAGA consists of a LPCI source and two mass filters in series, separated by a gas-collision region. Organic molecules in the sampled air stream are ionized directly at approximately 1 torr by the chemical reactions generated about a Townsend discharge electrode.

Unlike conventional electron ionization, in a mass spectrometer, the LPCI process is a "soft" and very efficient ionization process due to the high rate of molecular interactions; the result is very limited molecular ion fragmentation and the formation of predominantly intact molecular ions. The intact molecular ions of interest are isolated from other species in the matrix in the first mass filter, then focussed into the collision region containing neutral argon atoms. In this collision region, the molecular ion is fragmented with controlled energy into a few structurally characteristic ions of lesser mass. These fragment, or daughter, ions are separated by the second mass filter and are then detected. The entire process from sample introduction to detection takes place on the order of a few milliseconds, providing an instantaneous response to a dynamically changing atmosphere. In these studies, the TAGA was programmed to monitor $CCl_4$ and a new data point was recorded every 1.6 seconds.

PBPK Model

The PBPK model developed by Paustenbach et al. (1988) was modified for $CCl_4$ and to include multi-day exposure and modified to model the small metabolism chamber used to collect exhaled $^{14}CCl_4$. Model parameters are identical to those given by Paustenbach et al. (1988) except those adjusted to account for the smaller body weight of the animals used in the current studies. Model parameters are found in Table 1.

TABLE 1

| Model Parameters | |
|---|---|
| Body weight | 250 g |
| Tissue volume (percent total body weight)[a] | |
| Liver | 4 |
| Fat | 8 |
| Slowly perfused tissue | 74 |
| Rapidly perfused tissue | 5 |
| Tissue blood flow (percent cardiac output)[a] | |
| Liver | 25 |
| Fat | 4 |
| Slowly perfused tissue | 20 |
| Rapidly perfused tissue | 51 |
| Cardiac output (ml blood/min)[a] | 80.8 |
| Alveolar ventilation (ml air/min)[a] | 78.5 |

TABLE 1-continued

| Model Parameters | |
|---|---|
| Metabolism[a] | |
| $V_{maxc}$ | 13.8 µg $CCl_4$/min per kg |
| $K_m$ | 0.25 µg/ml |
| Partition coefficients | |
| Fat: Blood[b] | 79.4 |
| Slowly perfused: Blood[b] | 2.0 |
| Richly perfused: Blood[c] | 3.14 |
| Liver: Blood[b] | 3.14 |
| Blood: Air[b] | 4.52 |

[a]Paustenbach et al., 1988.
[b]Gargas et al., 1986b.
[c]Set equivalent to partition coefficient for liver: blood Equations to simulate the introduction of the $CCl_4$ through a jugular vein cannula directly into the mixed venous blood pool were included. The PBPK models were solved using SimuSolv (Dow Chemical Company, Midland, Mich.), a software package containing routines for numerical integration, optimization, and graphical display.

Results

Figure 3A:
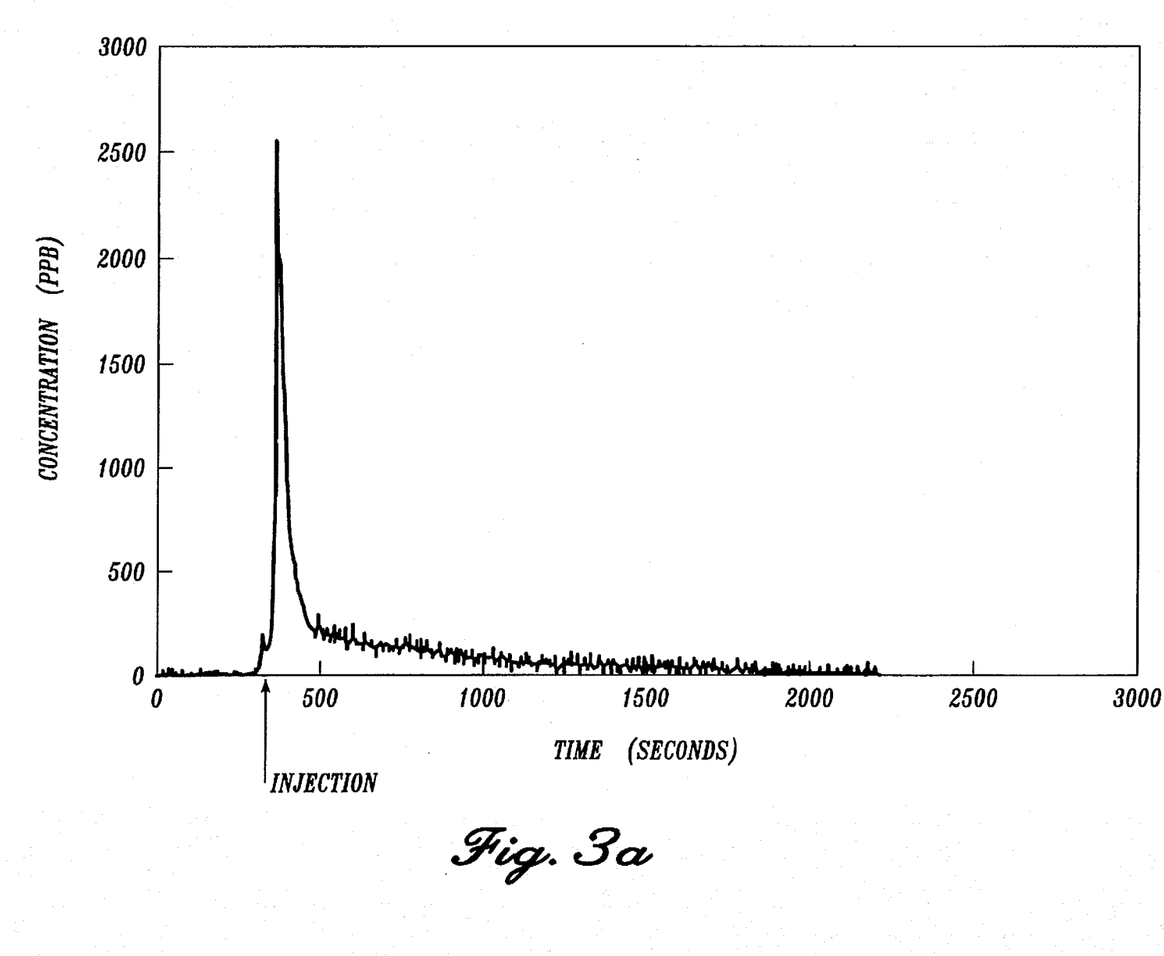
FIG. 3a. is a graph of real-time measurement of the combined exhalation of $CCl_4$ from two rats receiving a single intravenous injection of $CCl_4$ in isotonic saline at a dose of 0.6 mg/kg BW (250 µl volume) via the jugular vein.
Figure 3B:
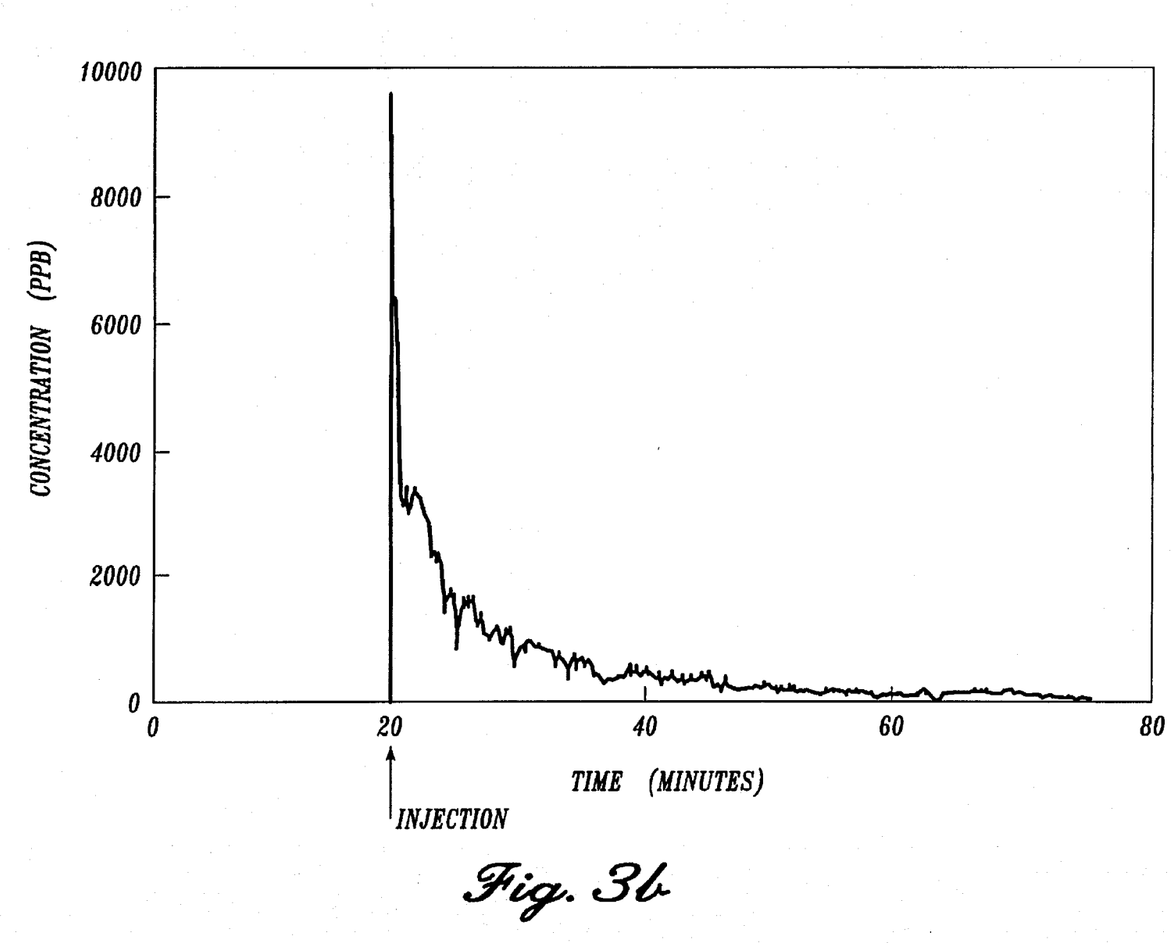
FIG. 3b is a graph of real-time measurement of the combined exhalation of $CCl_4$ from four rats receiving a single intravenous injection of $CCl_4$ in isotonic saline at a dose of 1.5 mg/kg BW (1 ml volume) via the tail vein.

The real-time measurement of the combined exhalation of $CCl_4$ from two and four rats, each receiving a single intravenous injection is shown in FIGS. 3a and 3b, respectively. A repeat of the 4-animal exposure experiment yielded results identical to those shown in FIG. 3b. Although the initial study utilized animals with indwelling jugular vein cannulas, subsequent studies used tail-vein injections for introduction of the $CCl_4$. Different dose introduction techniques, as well as the higher dose levels, were used in an attempt to detect any biomarkers of $CCl_4$-induced lipid peroxidation (specifically acetone) in the exhaled breath. From the end of the injection, peak concentration of $CCl_4$ in exhaled breath occurred in approximately 30 seconds. This is consistent with the calculated time delay of sample introduction into the inlet "tube" and travel to fill the common mixing chamber at the flow rate used here (28.5 seconds). As shown in both FIGS. 3a and 3b, the decay of the $CCl_4$ can be followed for 30–35 min after the injection before returning to the baseline established before the intravenous injection. Acetone was not detectable.

Figure 4A:
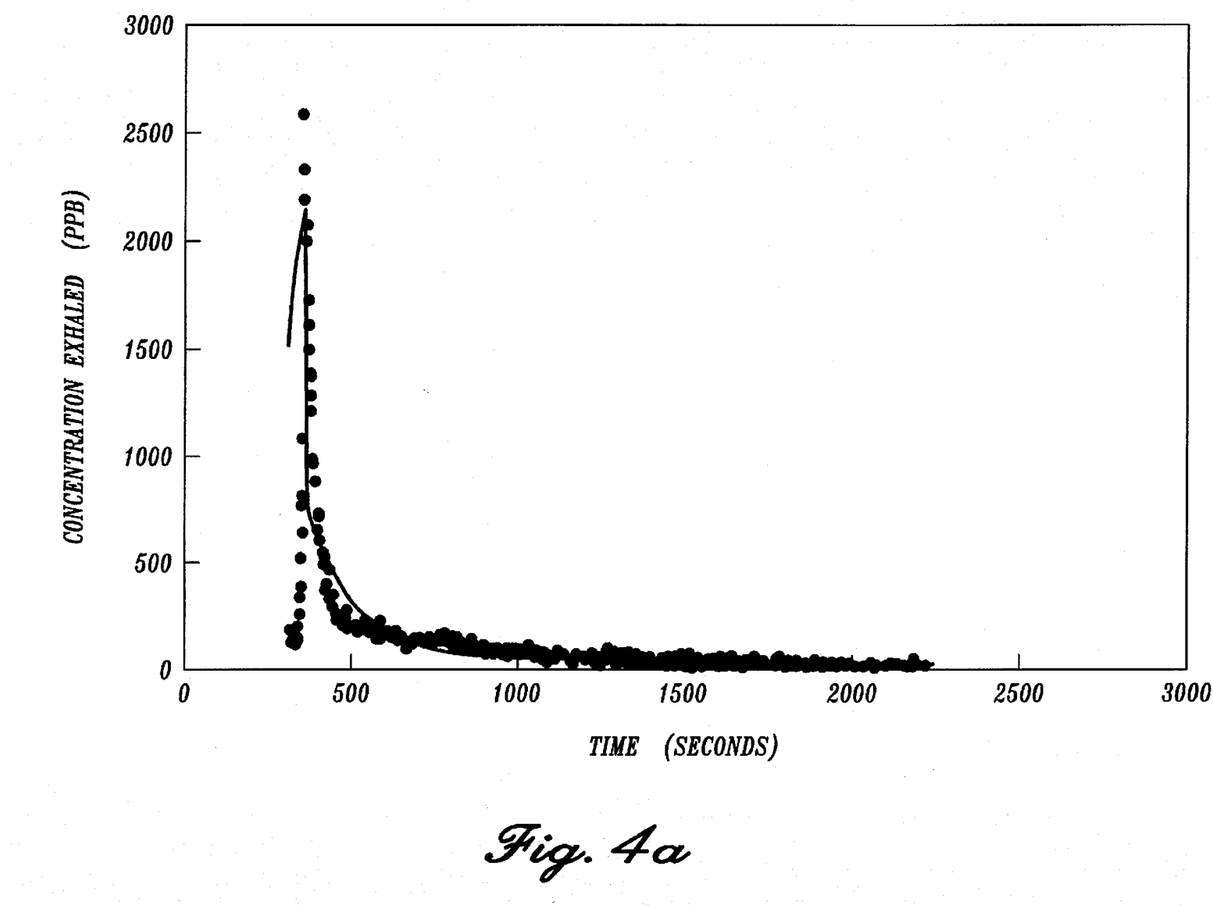
FIG. 4a. is a graph comparing the experimental data collected from two animals receiving a single intravenous injection of $CCl_4$ at a dose of 0.06 mg/kg via the jugular vein.
Figure 4B:
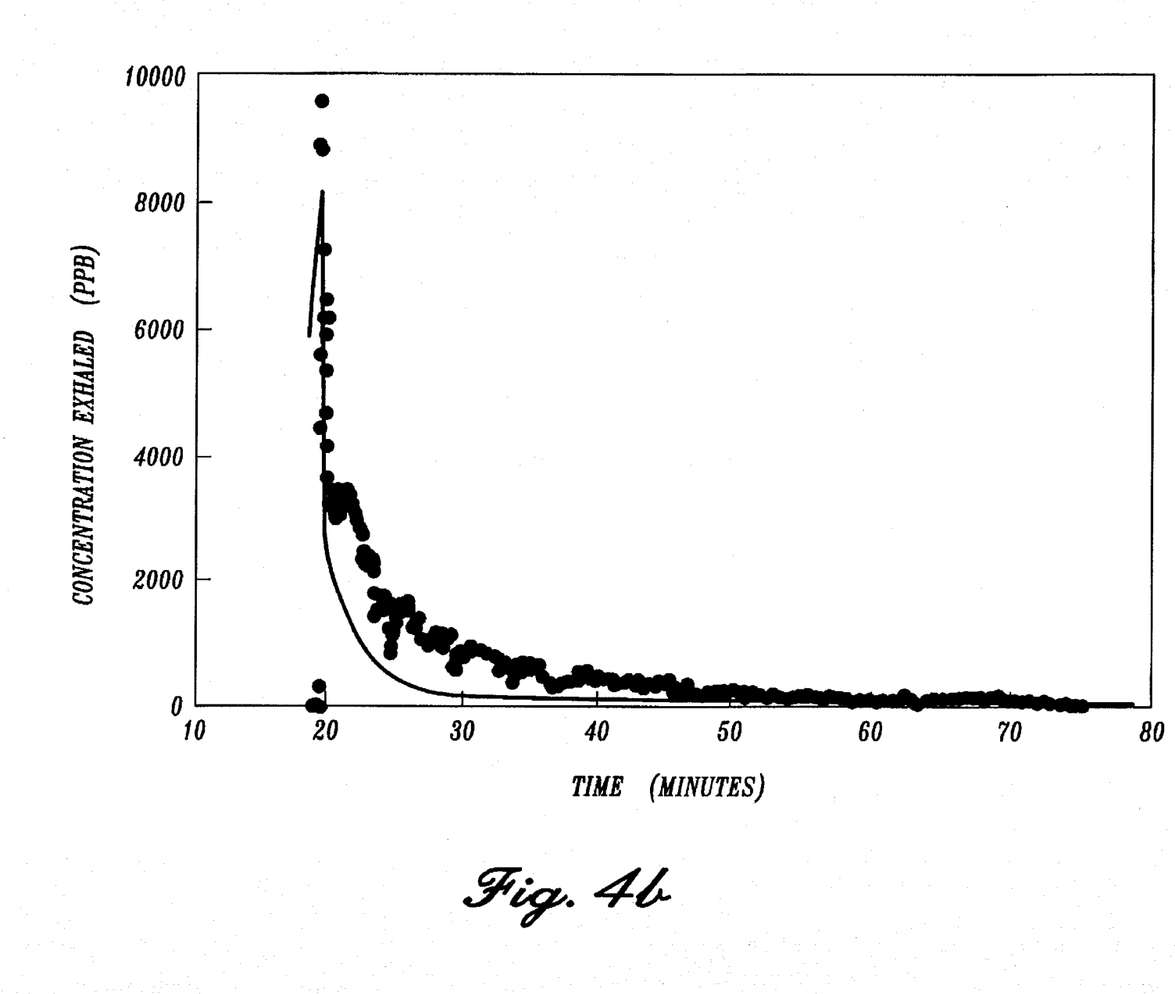
FIG. 4b. is a comparison of the experimental data collected from four animals receiving a single intravenous injection of $CCl_4$ at a dose of 1.5 mg/kg with the model prediction using the PBPK model.

The PBPK model was used to simulate an intravenous injection and compared against the measured exhaled concentration data. FIGS. 4a and 4b show solid line curves of the PBPK simulation superimposed upon the data points. The PBPK model predicted a more rapid elimination of $CCl_4$ in the group exposed via tail-vein injection than was observed for the animals exposed via jugular vein cannulation (FIG. 4a).

FIG. 3a clearly shows that the introduction of $CCl_4$ into the jugular vein via cannulation forces the compound to pass, nearly immediately, into the lung for an extremely rapid "first pass" elimination, with very low levels being available for subsequent distribution into the entire blood volume of the animal. On the other hand, FIG. 3b shows an initial sharp peak of compound eliminated through the lung, but a larger fraction of $CCl_4$ is held up in the circulating blood supply. A repeat of the study, again using 4 animals exposed via tail-vein injection, revealed the same elimination pattern as in FIG. 3b.

An advantage of using the breath analysis system according to the present invention is that the apparatus is transparent to the PBPK model. In other words, calibrating the mass spectrometer response to known concentration standards prepared in gas cylinders and introducing the standards into the system avoids the need to include the geometric parameters of the breath interface in the PBPK model. By varying the flow rate of the concentration standards and recording the mass spectrometric response, calibration curves and response factors are generated which include effects of any loss of an analyte within or from the mixing chamber.

Another advantage of the present invention is real-time sample collection permitting tracking of trends as a compound varies in concentration.

Closure

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

References

1. Arms, A. D., and Travis, C. C. 1988. Reference physiological parameters in pharmacokinetic modeling. EPA/600/6-88/004.
2. Dawson, P. H., French, J. B., Buckley, J. A., Douglas, D. J., and Simmons, D. (1982a). Mass spectrometry I: The instrument parameters. Org Mass Spectrom. 17, 205–211.
3. Dawson, P. H., French, J. B., Buckley, J. A., Douglas, D. J., and Simmons, D. (1982b). The use of triple quadrupoles for sequential mass spectrometry II: A detailed case study. Org Mass Spectrom. 17, 212–219.
4. Gargas, M. L., Andersen, M. E., and Clewell, H. J., III. (1986a). A physiologically based simulation approach for determining metabolic constants from gas uptake data. Toxicol. Appl. Pharmacol. 86, 341–352.
5. Gargas, M. L., Clewell, H. J., III, and Andersen, M. E. (1986b). Metabolism of inhaled dihalomethanes in vivo: Differentiation of kinetic constants for two independent pathways. Toxicol. Appl. Pharmacol. 82, 211–223.
6. Kenny, D. V., and Kelly, T. J. (August 1991). Apparatus and method for analysis of expired breath. U.S. Pat. No. 5,042,501.
7. Paustenbach, D. J., Clewell, H. J., III, Gargas, M. L., and Andersen, M. E. (1988). A physiologically based pharmacokinetic model for inhaled carbon tetrachloride. Toxicol. Appl. Pharmacol. 96, 191–211.
8. Ramsey, J. C., and Andersen, M. E. (1984). A physiologically based description of the inhalation pharmacokinetics of styrene in rats and man. Toxicol. Appl. Pharmacol. 73, 159–175.

We claim:

1. An apparatus for quantitatively assessing an exposure in terms of a total integrated exposure, dose, and predicted response of a person exposed to at least one hazardous chemical, said apparatus comprising:
   (a) a breath interface for receiving breath from a person;
   (b) an external exposure dosimeter interface for receiving a lapel tube from a person;
   (c) a chemical analysis device having at least one inlet port with at least one valve for receiving a first gas sample from said breath interface, and for receiving a second gas sample from said external exposure dosimeter interface; and
   (d) an electronic processor for controlling said valve(s) and for receiving data from said chemical analysis device and for analyzing said data at a rate of at least once per breath for assessing said exposure.

2. The apparatus as recited in claim 1, wherein said breath interface comprises:
   (a) a mouthpiece for interfacing a person to receive an exhaled breath;
   (b) a tube for carrying said exhaled breath from the mouthpiece to;
   (c) a mixing chamber having an inlet, outlet and exit tube, said mixing chamber providing a residence time sufficient to mix the exhaled breath and provide a sufficient exhaled breath sample amount to the chemical analysis device; and
   (d) a heating means for preventing condensation of vapor present in the breath sample.

3. The apparatus as recited in claim 1, wherein said external exposure dosimeter interface comprises:
   (a) a heating block having a chamber for receiving said lapel tube;
   (b) a desorption handle for holding the lapel tube in the heating block; and
   (c) a temperature controller for heating said heating block and said lapel tube; wherein
   (d) a purge gas is introduced through a purge line entraining chemical compounds from the heated lapel tube and entering a common inlet to said inlet port.

4. The apparatus as recited in claim 1, wherein said chemical analysis device is a mass spectrometer.

5. The apparatus as recited in claim 1, wherein said electronic processor performs said analyzing with a pharmacokinetic model thereby obtaining said total integrated exposure, said predicted response and an internal tissue dose.

6. A method for quantitatively assessing an exposure in terms of a total integrated exposure, dose, and predicted response of a person exposed to at least one hazardous chemical, said method comprising the steps of:
   (a) receiving a breath from a person into a breath interface;
   (b) receiving a lapel tube from an external exposure dosimeter interface;
   (c) passing said breath into a chemical analysis device having at least one inlet port with at least one valve for receiving a first gas sample from said breath interface, and for receiving a second gas sample from said external exposure dosimeter interface; and
   (d) obtaining analyses of said first gas sample at a rate of at least once per breath and analyses of said second gas sample from an electronic processor for controlling said valve(s) and for receiving data from said chemical analysis device and for analyzing said data for assessing said exposure.

7. The method as recited in claim 6, wherein receiving a breath comprises the steps of:
   (a) interfacing a person with a mouthpiece to receive an exhaled breath;
   (b) carrying said exhaled breath from the mouthpiece through a tube to a mixing chamber having an inlet, outlet and exit tube;
   (c) mixing said breath in said mixing chamber during a residence time sufficient to mix the exhaled breath and providing a sufficient exhaled breath sample amount to the chemical analysis device; and
   (d) heating said exhaled breath for preventing condensation of vapor present in the exhaled breath.

8. The method as recited in claim 6, wherein receiving a lapel tube comprises the steps of:

(a) heating a chamber containing said lapel tube;

(b) holding the lapel tube in the heating block;

(c) heating said heating block and said lapel tube; and (d) flowing a purge gas is through a purge line entraining chemical compounds from the heated lapel tube and entering a common inlet to said inlet port.

9. The method as recited in claim 6, wherein said chemical analysis device is a mass spectrometer.

10. The method as recited in claim 6, wherein at least once per breath is at least once per 1.6 seconds.

11. The method as recited in claim 6, wherein said analyzing is done with a pharmacokinetic model thereby obtaining said total integrated exposure, said predicted response and an internal tissue dose.

12. An apparatus for quantitatively assessing an exposure in terms of a total integrated exposure, internal tissue dose, and predicted response of a person exposed to at least one hazardous chemical, said apparatus comprising:

(a) a breath interface for receiving breath from a person;

(b) an external exposure dosimeter interface for receiving a lapel tube from a person;

(c) a chemical analysis device having at least one inlet port with at least one valve for receiving a first gas sample from said breath interface, and for receiving a second gas sample from said external exposure dosimeter interface;

(d) an electronic processor having a controller for controlling said valve(s) and an evaluator for receiving data from said chemical analysis device and for analyzing said data for assessing said exposure; wherein (e) said evaluator contains a pharmacokinetic model for analyzing data from both said breath interface and said external dosimeter interface and obtaining said total integrated exposure, internal tissue dose, and predicted response of said person exposed to said at least one hazardous chemical.

13. The apparatus as recited in claim 12, wherein said breath interface comprises:

(a) a mouthpiece for interfacing a person to receive an exhaled breath;

(b) a tube for carrying said exhaled breath from the mouthpiece to;

(c) a mixing chamber having an inlet, outlet and exit tube, said mixing chamber providing a residence time sufficient to mix the exhaled breath and provide a sufficient exhaled breath sample amount to the chemical analysis device; and (d) a heating means for preventing condensation of vapor present in the breath sample.

14. The apparatus as recited in claim 12, wherein said external exposure dosimeter interface comprises:

(a) a heating block having a chamber for receiving said lapel tube;

(b) a desorption handle for holding the lapel tube in the heating block; and (c) a temperature controller for heating said heating block and said lapel tube; wherein (d) a purge gas is introduced through a purge line entraining chemical compounds from the heated lapel tube and entering a common inlet to said inlet port.

15. The apparatus as recited in claim 12, wherein said chemical analysis device is a mass spectrometer.

16. A method for quantitatively assessing an exposure in terms of a total integrated exposure, internal tissue dose, and predicted response of a person exposed to at least one hazardous chemical, said method comprising the steps of:

(a) receiving a breath from a person into a breath interface;

(b) receiving a lapel tube from an external exposure dosimeter interface;

(c) passing said breath into a chemical analysis device having at least one inlet port with at least one valve for receiving a first gas sample from said breath interface, and for receiving a second gas sample from said external exposure dosimeter interface;

(d) analyzing said first and second gas samples with an electronic processor containing a pharmacokinetic model and obtaining said total integrated exposure, internal tissue dose, and predicted response of said person exposed to said at least one hazardous chemical.

17. The method as recited in claim 16, wherein receiving a breath comprises the steps of:

(a) interfacing a person with a mouthpiece to receive an exhaled breath;

(b) carrying said exhaled breath from the mouthpiece through a tube to a mixing chamber having an inlet, outlet and exit tube;

(c) mixing said breath in said mixing chamber during a residence time sufficient to mix the exhaled breath and providing a sufficient exhaled breath sample amount to the chemical analysis device; and (d) heating said exhaled breath for preventing condensation of vapor present in the exhaled breath.

18. The method as recited in claim 16, wherein receiving a lapel tube comprises the steps of:

(a) heating a chamber containing said lapel tube;

(b) holding the lapel tube in the heating block;

(c) heating said heating block and said lapel tube; and (d) flowing a purge gas is through a purge line entraining chemical compounds from the heated lapel tube and entering a common inlet to said inlet port.

19. The method as recited in claim 16, wherein said chemical analysis device is a mass spectrometer.

20. The method as recited in claim 16, wherein said analyses are obtained as often as of at least once per breath.

21. The method as recited in claim 20, wherein at least once per breath is at least once per 1.6 seconds.

* * * * *